United States Patent
Breysse

(10) Patent No.: US 9,668,823 B2
(45) Date of Patent: Jun. 6, 2017

(54) DENTAL TOOL WITH PENETRATION INDICATING BANDS

(71) Applicant: Pascal Breysse, St. Germain/L'Arbresle (FR)

(72) Inventor: Pascal Breysse, St. Germain/L'Arbresle (FR)

(73) Assignee: BIOTECH DENTAL, Salon de Provence (FR)

( * ) Notice: Subject to any disclaimer, the term of this patent is extended or adjusted under 35 U.S.C. 154(b) by 130 days.

(21) Appl. No.: 14/549,881

(22) Filed: Nov. 21, 2014

(65) Prior Publication Data

US 2015/0147715 A1 May 28, 2015

(30) Foreign Application Priority Data

Nov. 25, 2013 (FR) ..................................... 13 61613

(51) Int. Cl.
| | |
|---|---|
| *A61C 3/02* | (2006.01) |
| *A61C 8/00* | (2006.01) |
| *A61C 19/04* | (2006.01) |
| *A61B 17/16* | (2006.01) |

(52) U.S. Cl.
CPC ............ *A61C 3/02* (2013.01); *A61B 17/1673* (2013.01); *A61C 8/0089* (2013.01); *A61C 19/04* (2013.01)

(58) Field of Classification Search
CPC ....... A61B 17/1673; A61C 19/04; A61C 3/02; A61C 8/0089
See application file for complete search history.

(56) References Cited

U.S. PATENT DOCUMENTS

| | | |
|---|---|---|
| 5,299,937 A | 4/1994 | Gow |
| 6,364,662 B1 | 4/2002 | Kumar |
| 2003/0049586 A1 | 3/2003 | Kumar |
| 2007/0101827 A1 | 5/2007 | Quan et al. |
| 2012/0330315 A1* | 12/2012 | Ranck ................ A61B 17/1615 606/80 |

FOREIGN PATENT DOCUMENTS

| | | |
|---|---|---|
| EP | 1 128 777 | 10/2007 |
| KR | 2012 0096839 | 8/2012 |

OTHER PUBLICATIONS

French Search Report dated Jul. 14, 2014, corresponding to the Foreign Priority Application No. 1361613.

* cited by examiner

*Primary Examiner* — George Manuel
(74) *Attorney, Agent, or Firm* — Young & Thompson

(57) ABSTRACT

A dental instrument 1 adapted for performing osteotomy includes a mounting shank 2 and, in line therewith, a working portion 3 including cutting zones 3A, of which at least part is covered by a coating of carbon-enriched tungsten carbide except for a plurality of annular bands 10 distributed along the length of the working portion to indicate the depth of penetration of the tool into a portion of jaw.

14 Claims, 1 Drawing Sheet

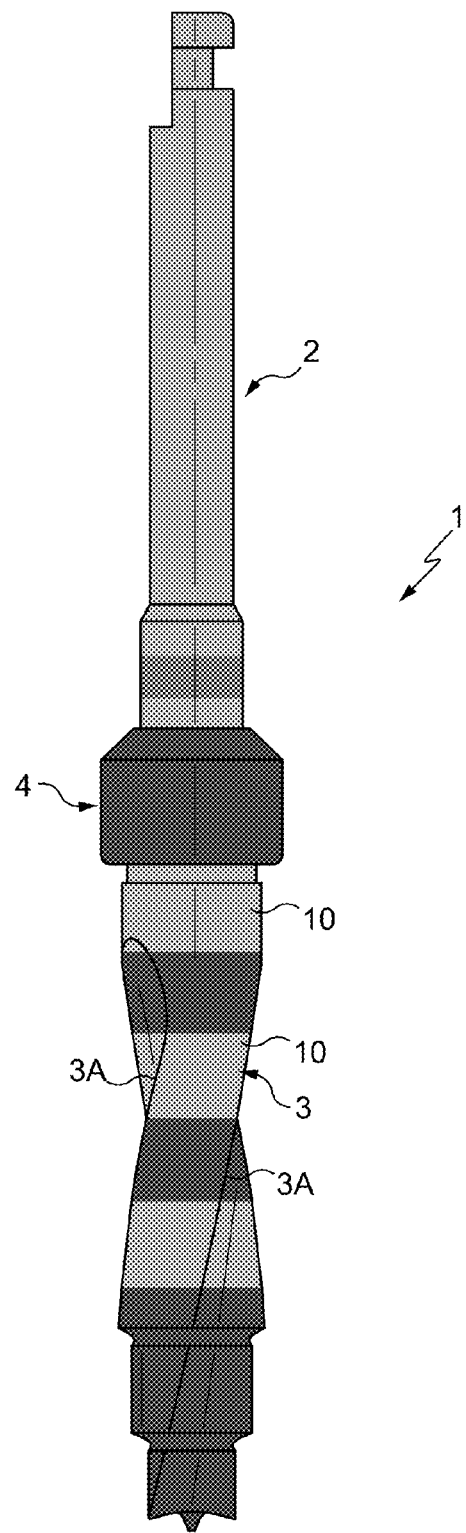

DENTAL TOOL WITH PENETRATION INDICATING BANDS

FIELD OF THE INVENTION

The invention relates to a dental instrument, of drill bit, milling cutter or reamer type, of which the working surface comprises a hard, wear-resistant coating.

BACKGROUND OF THE INVENTION

Such an instrument is conventionally elongate with a shank adapted to be engaged in a manual or motorized rotational drive apparatus, and a working part of which the working surface, extending from one end, provides the drilling or boring function.

As is known, a dental operation such as osteotomy, generally involves forming or enlarging a channel in the jawbone, sometimes using a an instrument rotationally driven at high speed, and it generally required of such a dental instrument to have a low coefficient of friction with the jawbone (which is promoted by the presence of lubrication, sometimes through the instrument), a high mechanical hardness conferring good wear resistance, good corrosion resistance, in particular to the acids of saliva, and good thermal conductivity to efficiently remove the heat generated when drilling a channel, while being biocompatible.

To meet such a combination of needs, it has been proposed, in particular by document U.S. Pat. No. 5,299,937, to cover at least the working surface of a dental instrument with a diamond type hard carbon coating (often referred to as DLC, standing for Diamond-Like-Carbon); more recently, the document EP-1 128 777 recommended selecting such a diamond-like-carbon coating containing between 5 at. % and 35 at. % hydrogen.

In fact, when a dental instrument is used for osteotomy, manipulated by hand or actuated by a rotational drive motor, it is useful to be able to evaluate as precisely as possible the depth to which the end of the instrument has reached in the bone. It was to meet that need that it was proposed, in particular in the aforementioned document EP-1 128 777, to form visible depth markers on the working surface of the instrument, such as annular bands surrounding the working part of the instrument that are produced so as to form a visible contrast with the rest of the surface of that working part; in practice these depth bands are formed by locally removing the whole of or part of the thickness of the diamond-like-carbon coating. In practice, these bands are equidistant; furthermore, there are instruments on which the bands are of a width substantially equal to the distance separating them.

Such a configuration is satisfactory in numerous cases but it has been found that, in certain orientations, during certain operations, the visible contrast between the depth bands becomes insufficient to enable reliable evaluation of the depth which the end of the instrument used has reached.

SUMMARY OF THE INVENTION

The invention relates to a dental instrument, adapted for osteotomy operations, meeting the various constraints applying to such an instrument, in particular those set forth above, while presenting improved contrast relative to that given by a diamond-like-carbon (DLC) coating.

To that end the invention provides a dental instrument adapted for performing osteotomy comprising a mounting shank and, in line therewith, a working portion comprising cutting zones, of which at least part is covered by a coating of carbon-enriched tungsten carbide except for a plurality of annular bands distributed along the length of the working portion to indicate the depth of penetration of the tool into a portion of jaw.

In a way which is most surprising, it has been found that carbon-enriched tungsten carbide enables better detection of the annular bands than DLC even though carbon-enriched tungsten carbide is less black than DLC (DLC is a dark black whereas carbon-enriched tungsten carbide, designated hereinafter by the acronym CETC, is a dark gray). In fact, it was initially assumed that, to improve the contrast between the annular bands and the coating, it was necessary to increase the color difference between those annular bands and the coating; it was nevertheless found that this visible contrast could be improved with CETC, despite a smaller color difference, due to the fact that this coating is mat whereas DLC may give reflections in certain lighting configurations. In other words, to improve the detection of the annular bands, it could be more effective to seek to obtain a large difference in appearance (shine or brilliance) rather than a maximization of the color difference; the contrast could be improved from the point of view of color but also and especially from the point of view of brilliance.

Advantageously, the coating is of a thickness comprised between 1 and 5 micrometers, or even between 1 and 3 micrometers for example at least approximately equal to 2 micrometers.

According to another advantageous feature of the invention, the annular bands are equidistant; furthermore, they preferably have a longitudinal dimension equal to their separation.

Independently of the longitudinal dimension of the bands, their separation is preferably comprised between 1 and 3 mm, for example 2 mm; by analogy, independently of the longitudinal dimension of the separations between the bands (which may vary from one location to another), the longitudinal dimension of the bands is advantageously comprised between 1 and 3 mm, for example equal to 2 mm.

BRIEF DESCRIPTION OF THE DRAWINGS

Objects, features and advantages of the invention will appear from the following description, given by way of illustrative non-limiting example, with reference to the appended drawing on which the single FIG. 1 represents a dental instrument in accordance with the invention.

DETAILED DESCRIPTION OF THE INVENTION

As is usual, the dental instrument 1 is elongate, generally cylindrical and with a diameter very much less than its length.

In the example considered here, the dental instrument is a drill bit, but it may, as a variant, be in particular a reamer, a thread-cutter, in particular, or any other instrument able to participate in an osteotomy operation.

This drill bit comprises, in conventional manner, a shank 2 adapted to be engaged in a tip of a high-speed rotational drive device, and a working portion 3 comprising cutting zones 3A (here edges) extending longitudinally, which are advantageously helical; these zones stopping here at a slight distance from the end of the working portion, which is of a smaller diameter than the part in which those cutting zones are formed.

An increased thickness 4 is formed here between the shank 2 and the working part 3.

According to the invention, at least part of the working portion bears a coating of carbon-enriched tungsten carbide, or CETC.

Preferably, this coating extends from the end of the working portion to the separation (near the annular increased thickness 4) between that working portion and the shank. In other words, this coating extends over practically the whole length of the working portion. As a variant, it can extend only over a fraction (in practice of at least 50%, preferably at least 75%) of that length.

Preferably, in the example represented, this coating covers not only the outside surface of the working portion but also the inside of the zones that are recessed towards the axis relative to the cylindrical shape the tool has locally, that is to say in the zones located alongside the cutting edges. As a variant, it is possible for the whole of or part of these zones not to be covered by that coating.

Although the coating extends over a substantial fraction of the length of the working portion, it is discontinuous on account of the presence of annular bands 10 where that coating is not present (or almost not present). The surface of these bands is thus very slightly recessed relative to the outside surface of the zones in which the coating is present, by hardly the thickness of the coating.

These bands are here disposed regularly, starting from a certain distance from the end (as a matter of fact the end portion of the working portion is entirely coated).

These bands here are of a length (that is to say a dimension parallel to the length of the tool) at least approximately equal to their longitudinal separation, such that each of the edges of these bands per se constitutes a depth indicating marker; these bands here are of length 2 mm and of spacing 2 mm. As a variant, the longitudinal dimension of the bands may vary from one band to another, while advantageously being comprised between 1 mm and 3 mm (bounds included); similarly, the longitudinal dimension of the spacings may vary from one spacing to the other, while advantageously being comprised between 1 and 3 mm; these are values enabling good distinction between the successive bands, while enabling good detection of the band not to go beyond in a given application.

These bands 10 present a contrast with the coated portions due to the fact that the material constituting the working portion of the tool has a high contrast with the CETC coating.

These bands may be obtained by depositing that coating only on the narrow end of the working part and between the light bands 10; it is however easier to proceed by depositing the coating over the entirety of the light and dark zones of the working portion, then to selectively remove the coating at the location of the bands 10.

The coating may be deposited by any appropriate known technique, for example by vapor phase deposition (or CVD, acronym for "Chemical Vapor Deposition"). This is a deposit in a thin layer, for example carried out in a vacuum of the order of $10^{-2}$ bars based on a tungsten carbide target, adding thereto an ionized carbon-containing gas which confers the carbon-enriched character to the coating.

This coating is advantageously of a thickness comprised between 1 and 5 micrometers, preferably between 1 and 3 micrometers, for example substantially equal to 3 micrometers.

The successive removal of this coating, at the location of the future light bands 10, may be carried out by chemical or mechanical ablation, or by laser ablation. In particular, laser ablation enables the coating to be removed not only on the outside surface of the working portion but also inside the flutes located alongside the cutting edges.

Surprisingly, it has appeared that a dental tool so coated with CETC led to friction characteristics entirely comparable with those of a dental tool coated with DLC hard carbon, while giving better wear resistance and above all giving better visible contrast between the coated dark bands and the light bands.

In their approach directed to developing a dental tool having a better contrast between the depth indicating bands and the rest of the coating, the inventors started out initially on the premise that a coating at least as dark as DLC was required, even though DLC is known to have a dark black color.

The inventors thus sought to identify another coating having a strongly black color; this led them to take an interest in an alloy of AlTiN titanium aluminum nitride type, by testing several shades available on the market.

It was found that the ablation of the coating at the locations of the bands to be made light was, according to the tested shades, effective or ineffective, which led to testing shades that were difficult to ablate without using a binding layer, or with a chromium-based binding layer.

With a conventional binding layer (TiN, of thickness typically equal to 0.2 micrometers), it was found that, on the ablated zones, there remained a yellow hue arising from the fact that the laser ablation burned that binding layer; it was for this reason that a chromium-based binding layer was attempted to be used, making a silvered hue appear which was closer to the hue of the bare dental tool. The coating remained, overall, biocompatible, but this silver hue did not make it possible to have a better contrast than with DLC. In the absence of a binding layer, the mechanical strength of the coating was insufficient.

One of the reasons why the insufficient contrast was attributed to that AlTiN alloy was that this material is more gray than black.

When it was envisioned to test a CETC coating, there was initially a negative prejudice on account of this material being known not to have mechanical properties as good as DLC; in this connection reference may be made to the document U.S. Pat. No. 5,299,937 which, in relation to the advantage of a coating of DLC type, takes the example of a tool of tungsten carbide; furthermore, this material prima facie had the same drawback as titanium-aluminum nitride, i.e. that of having a hue that is more gray than black. Lastly, tungsten carbide was known often to contain cobalt (on account of its role as a binder, in an amount of a few percent), which prima facie made it incompatible with applications requiring biocompatibility. Lastly, the hardness of tungsten carbide is less than that of DLC, especially hydrogenated DLC (1500 HV as against 2200 HV). All of this thus led to concluding that this coating was prima facie unsuitable for the application in which it was sought to obtain a better contrast than with DLC.

However, when it was accepted to actually conduct tests, it was found that current shades of tungsten carbide do not contain cobalt especially after vacuum deposition (of CVD type, see above) and, after having adapted the conditions for ablating the coating on the basis of that material, the visible contrast between the ablated bands and the coated bands turned out to be better, in a high number of cases, than with DLC; furthermore, the CETC coating turned out to have a higher wear resistance than the DLC, which appeared to be in contradiction with the fact that it was less hard than that material. Lastly, that material turned out to be biocompatible.

In fact, it would seem that the CETC very rarely gives rise to reflections despite the strength of the lighting by operating-theatre lamps; to be precise, that coating has a mat appearance. Furthermore, the ablation of this coating does not lead to any yellowing of the ablated surface such that those surfaces are lighter than the ablated zones with a material such as AlTiN. Strictly speaking, such a CETC coating has, relative to the underlying surface (in practice the surface of a stainless steel), a color difference less than that obtained with DLC, but the impression of a better contrast comes from the mat appearance of the coating which makes it possible to maintain the detectability of the light bands in all the lighting configurations, which is not the case with DLC of which the appearance is sometimes brilliant to the extent of giving reflections.

It should be noted that, although it had been proposed to use laser ablation to form the light bands to be formed on a dental tool provided with a DLC coating (see for example the document EP-1 128 777), it turned out that in practice (probably for reasons of technical difficulty or cost) such light bands are obtained by means of mechanical machining, which can be recognized due to the fact that the coating remains intact in the flutes located alongside the cutting edges (hence a lower visibility of the light bands); yet such machining, if it is desired to ensure total removal of the coating to obtain a good color contrast, necessarily penetrates the material of the tool, even if this is by a few tens of microns, with the risk of locally removing the corrosion-protection layer and forming failure initiations leading to risks of breakage of the tool in use, which may prove to be unacceptable; to this the fact is to be added that the steps generated by such machining generate a risk of detachment of the coating when the dental tool is in use. Yet it turned out that, with a CETC coating, laser ablation enabled that coating to be eliminated efficiently, including in the flutes located alongside the cutting edges, without degrading the material from the point of view of corrosion resistance or mechanical strength properties in particular in bending. It is within the capability of the person skilled in the art to define operational conditions for such ablation on the basis of the underlying material, in practice a stainless steel.

However, the deposit of a CETC is carried out at a temperature greater than that of the deposit of a DLC (of the order of 400° C. as opposed to of the order of 200° C.) with a technique generally involving more energy than the DLC deposit (in PACVD, standing for "Plasma Assisted Chemical Vapor Deposition"), which would lead it to be assumed that the deposit of CETC would be more difficult to ablate than the DLC coating. Nevertheless, it would appear that, in the envisioned application, there is a synergy between the predictable drawbacks of the CETC coating, i.e. that the high deposit temperature of the CETC coating leads to better attachment of that coating onto the surface of the tool; it follows that this coating has better wear resistance than DLC; in parallel, the fact that CETC is less hard than DLC means that is easier to ablate than DLC without yellowing or tarnishing of the underlying surface, hence the final combination of properties which contrary to what could have been predicted, is better with CETC than with DLC. It may be added that the fact that the wear of the CETC coating is slower than that of DLC has the advantage of maintaining the cutting quality of a tool provided with the coating of the invention for longer relative to a tool coated with DLC.

CETC has a coefficient of friction of 0.15, as compared with the value of 0.1 for DLC, which does not constitute a decisive difference and the CETC has a thermal conductivity comparable to that of DLC.

It may be noted that CETC has a metallic structure (that of tungsten carbide) whereas a coating such as that recommended in the prior art, that is to say DLC, has an amorphous structure.

It can easily be understood that the above comments apply not only to a drill bit as represented but to other types of dental tool that may be used in osteotomy.

The invention claimed is:

1. A dental instrument adapted for performing osteotomy comprising:
   a mounting shank (2), and
   in line with the mounting shank (2), a working portion (3) comprising cutting zones (3A), at least part of the cutting zones (3a) being covered by a coating of carbon-enriched tungsten carbide except for a plurality of annular bands (10) distributed along the length of the working portion to indicate the depth of penetration of the tool into a portion of jaw, the annular bands being recessed relative to an outside surface of the cutting zones in which the coating is present by hardly a thickness of the coating.

2. A dental instrument according to claim 1, wherein the coating is of a thickness comprised between 1 and 5 micrometers.

3. A dental instrument according to claim 2, wherein the annular bands are equidistant.

4. A dental instrument according to claim 3, wherein the annular bands have a longitudinal dimension equal to their separation.

5. A dental instrument according to claim 2, wherein, each separation between two successive annular bands is comprised between 1 and 3 mm.

6. A dental instrument according to claim 2, in which the longitudinal dimension of each band is advantageously comprised between 1 and 3 mm.

7. A dental instrument according to claim 1, wherein the annular bands are equidistant.

8. A dental instrument according to claim 7, wherein the annular bands have a longitudinal dimension equal to their separation.

9. A dental instrument according to claim 1, wherein, each separation between two successive annular bands is comprised between 1 and 3 mm.

10. A dental instrument according to claim 1, in which the longitudinal dimension of each band is advantageously comprised between 1 and 3 mm.

11. A dental instrument according to claim 1, wherein the annular bands are recessed, relative to the outside surface of the cutting zones in which the coating is present, by only the thickness of the coating.

12. A dental instrument according to claim 1, wherein the annular bands are recessed, relative to the outside surface of the cutting zones in which the coating is present, by only the thickness of the coating, and the coating of carbon-enriched tungsten carbide has a mat surface.

13. A dental instrument adapted for performing osteotomy, comprising:
   a mounting shank (2);
   a working portion (3) in line with the mounting shank (2), the working portion (3) comprising cutting zones (3A),
   a first group of the cutting zones (3a) being covered by a coating of carbon-enriched tungsten carbide having a mat surface, and a second group of cutting zones (3a)

not being covered by the coating of carbon-enriched tungsten carbide, the coating having a thickness, each of the cutting zones of the second group being shaped as an annular band (10) distributed along the length of the working portion to indicate the depth of penetration of the tool, and each of the annular bands being adjacent one of the cutting zones (3*a*) of the first group and an outside surface of each of the annular bands being recessed relative to an outside surface of the adjacent one of the cutting zones (3*a*) of the first group by only the thickness of the coating.

14. A method of providing a dental instrument, comprising the steps of:

providing a mounting shank (2) and, in line with the mounting shank (2), a working portion (3) comprising cutting zones (3A);

coating a part of the working portion with a coating of carbon-enriched tungsten carbide; and selectively removing the coating so as to form a plurality of uncoated annular bands distributed along a length of the working portion, the uncoated annular bands to indicate a depth of penetration of the tool into a portion of a jaw, the annular bands being recessed relative to an outside surface of the cutting zones in which the coating remains present by the removed thickness of the coating.

\* \* \* \* \*